United States Patent [19]

Newton

[11] 4,387,187

[45] Jun. 7, 1983

[54] COMPATIBLE POLYMER BLEND COMPOSITIONS

[75] Inventor: Alan B. Newton, Welwyn Garden City, England

[73] Assignee: Imperial Chemical Industries Limited, London, England

[21] Appl. No.: 242,403

[22] Filed: Mar. 10, 1981

[30] Foreign Application Priority Data

Mar. 25, 1980 [GB] United Kingdom ................. 8010073

[51] Int. Cl.$^3$ ...................... C08L 71/02; C08L 81/06
[52] U.S. Cl. .................................. 525/409; 525/403; 525/410; 525/523; 525/535
[58] Field of Search ................. 525/403, 409, 410, 523

[56] References Cited

U.S. PATENT DOCUMENTS

| | | | |
|---|---|---|---|
| 3,629,170 | 12/1971 | Kobe et al. | 524/93 |
| 4,208,508 | 6/1980 | Hashino et al. | 528/174 |

FOREIGN PATENT DOCUMENTS

| | | | |
|---|---|---|---|
| 2176118 | 10/1973 | France . | |
| 48-08860 | 3/1973 | Japan | 525/403 |
| 50-089475 | 7/1975 | Japan . | |
| 54-026283 | 2/1979 | Japan . | |
| 1416144 | 12/1975 | United Kingdom . | |
| 1416643 | 12/1975 | United Kingdom . | |
| 2020299 | 11/1979 | United Kingdom . | |

*Primary Examiner*—Wilbert J. Briggs, Sr.
*Attorney, Agent, or Firm*—Cushman, Darby & Cushman

[57] ABSTRACT

A polymer composition in the form of a film which composition comprises a compatible blend of an alkylene oxide polymer such as polyethylene oxide and an aromatic polyethersulphone.

10 Claims, No Drawings

COMPATIBLE POLYMER BLEND COMPOSITIONS

The present invention relates to a polymer composition in the form of a film and comprising a compatible polymer blend.

Alkylene oxide polymers, i.e. polymers comprising divalent alkylene groups bridged by ether linkages, are well known, many examples of them being commercially available. For example, polyethylene oxide resins are commercially available materials, varying in molecular weight from about 1000 to several million. The lower molecular weight polyethylene oxide resins (molecular weight e.g. 1,500–20,000) are greases and waxes while the higher molecular weight resins (molecular weight e.g. $\geqq 100,000$) are water-soluble, often crystallisable, solids of low softening point (about 65°–70° C.).

Aromatic polyethersulphone resins are also commercially available materials and are particularly characterised by their high softening point (usually >180° C.) and by being amorphous. Their molecular weights are usually such that useful polymers have reduced viscosity (RV) of at least 0.25. (RV as used herein refers to viscosity measurements made at 25° C. on a solution of the polyethersulphone in dimethyl formamide containing 1 g of polymer in 100 cm$^3$ of solution.)

It is known that most polymeric blends of two or more polymers are incompatible. However in British Pat. No. 1 416 144 it is disclosed that a wide range of diverse thermoplastic polymers, including aromatic polysulphones, are able to form compatible blends with cyclic ester polymers (i.e. polymers derived by polymerising cyclic esters), these cyclic ester polymers optionally containing up to 95% by weight of copolymerised alkylene oxide units. It is taught in British Pat. No. 1 416 144 that it is the presence of the cyclic ester polymer which lessens phase separation and hence incompatibility.

According to the present invention there is provided a polymer composition in the form of a film which composition comprises a compatible blend of an alkylene oxide polymer not containing units derived from a cyclic ester and an aromatic polyethersulphone.

It has been discovered that alkylene oxide polymers (not containing units derived from a cyclic ester) and aromatic polyethersulphones can form compatible blends with each other. This is a most surprising discovery since the solubility parameters of the two types of polymers are significantly different so that, in the absence of units derived from a cyclic ester to impart compatibility, very heterogeneous blends might have been expected. By a compatible polymer blend is meant a blend in which the polymers are entirely miscible so as to form a single phase, or a blend in which the phase separation has only occurred to a minor extent so that desirable blend properties are not deleteriously affected.

The compatibility of the polymers in the blends allows the polymer blends to provide the basis of useful compositions in the form of films. The films are preferably made by conventional solvent casting techniques; production by melt fabrication is not recommended since degradation and/or phase separation may occur.

It is of course to be understood that two or more alkylene oxide polymers as well as one alkylene oxide polymer, and similarly two or more polyethersulphones as well as one polyethersulphone, can comprise the polymer compositions of the invention.

In one embodiment of the invention, useful transparent films can be made even though the refractive indices of the alkylene oxide polymer and aromatic polyethersulphone are usually quite different.

Where the alkylene oxide component of the composition is water-soluble (e.g. high molecular weight polyethylene oxide), the films according to the invention exhibit a high wettability to water, having for example a contact angle of their surfaces to water of $\leqq 60°$ as measured using a reflecting goniometer device. Surprisingly, such films, unless deliberately treated to provide a porous structure therein, do not appear to actually absorb water and may e.g. be steeped in cold, warm or even boiling water without any appreciable uptake of water. This is perhaps due to a specific interaction between the polymeric components in the composition. However it is possible to prepare a porous or semi-permeable film according to the invention prior to the formation of such a non-water absorbing film (or prior to the formation of any non-water absorbing film comprising a compatible blend of an alkylene oxide polymer as defined and an aromatic polyethersulphone) by leaching the film, which has been prepared by solvent casting and still contains some of the solvent medium used in the casting, with a liquid which is miscible with at least one component of the solvent casting medium and is also a non-solvent for the polymers of the blend. Thus, for example, such a film may be prepared by leaching with water a film which has been formed by casting from a water-miscible solvent such as dimethyl formamide and/or N-methyl pyrrolidone and still contains some of the solvent. Possible uses for such films are in the field of membrane separation technology (e.g. ultra-filtration or reverse osmosis). Another possible use is in the field of sustained and/or predictable release in unit dosage form of biologically (e.g. pharmaceutically) active species (e.g. medicinal drugs) where the sustained and/or predictable release of the species in unit dosage form may be effected by means of the encapsulation thereof with a porous or semi-permeable membrane according to the invention.

The use of porous or semi-permeable films according to the invention for membrane technology, particularly in the field of sustained and/or predictable release of biologically (e.g. pharmaceutically) active species in unit dosage form, is additionally advantageous in that films according to the invention do not appear to be deleteriously affected by boiling water, boiling dilute acid or boiling dilute alkali which allows the possibility of facile sterilization. Also the effectiveness of porous or semi-permeable films according to the invention for membrane technology will be enhanced by the excellent water wettability of films according to the invention.

By alkylene oxide polymers are meant in this specification homopolymers or copolymers derived from the homopolymerisation of alkylene oxides or the copolymerisation of alkylene oxides with other monomers copolymerisable therewith (apart from the restriction concerning the use of cyclic esters). It is to be understood that the alkylene groups are unsubstituted, i.e. do not have substituents such as halogen or hydroxyl. Accordingly polymers such as poly(epihalohydrins), polyhydroxy ethers and epoxy resins are not examples of alkylene oxide polymers according to the invention. The preparation of alkylene oxide polymers used in the invention is well described in the literature, e.g. in "High Polymers", Vol XIII, (Polyethers, Part 1, Polyalkylene Oxides and Other Polyethers), Ed. Gaylord, Interscience, 1963—the polymers usually being made using acid or base catalysis. Examples of such polymers are those derived from the homo-or copolymerisation of ethylene oxide, propylene oxide or tetrahydrofuran to form, respectively, polyethylene oxides, polypropylene oxides, or poly (tetramethylene) oxides. Where the alkylene oxide polymer is a copolymer, the ether repeat unit derived from the alkylene oxide monomer may be arranged in a random fashion, in a block fashion, in a grafted fashion, or (with the other comonomer unit or units) in an alternating fashion. Preferably the alkylene oxide copolymer contains at least 50 mole % of units derived from alkylene oxide. In addition to copolymers of alkylene oxides with other types of monomers, copolymers of an alkylene oxide with one or more different alkylene oxides (e.g. ethylene oxide/propylene oxide copolymers) are also envisaged and may be of particular use.

The polyethylene oxide resins used in the present invention are preferably of high molecular weight (e.g. molecular weight at least 100,000, for example in the range 100,000 to 4,000,000). If low molecular weight polyethylene oxides are used (e.g. molecular weight below 20,000) it is preferable that the terminal —OH groups are capped, e.g. by methyl groups, as it is suspected that the presence of free —OH groups can induce blend heterogeneity. The polyethylene oxide resins may be advantageously prepared on a commercial scale by controlled polymerisation of ethylene oxide under alkaline conditions.

The aromatic polyethersulphones used in the invention comprise repeat units of the general formula —Ar—SO$_2$— in which Ar is a divalent aromatic radical, which may vary from unit to unit in the polymer chain, at least some of the Ar units having the structure

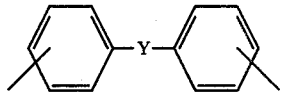

in which Y is oxygen or the divalent radical having the structure of an aromatic diol in which the hydrogen atoms of the nuclear —OH groups are removed.

Preferred examples of such polyethersulphones have the repeat units

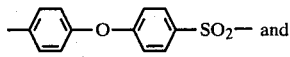 and

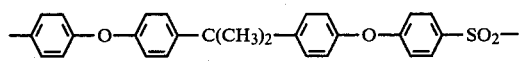

alone or in conjunction with repeating units, such as

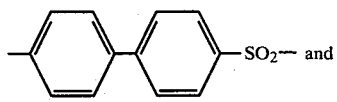 and

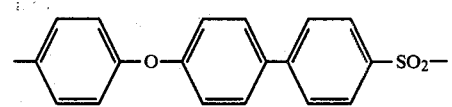

The aromatic polyethersulphones may e.g. be made by a nucleophilic condensation process in which an alkali metal halophenate (made by reacting e.g. a dihalobenzenoid compound and an alkali metal hydroxide), or a mixture of substantially equimolar proportions of an alkali metal bisphenate (or bisphenol plus alkali metal carbonate or bicarbonate) and a dihalobenzenoid compound, in which halophenate or dihalobenzenoid compound each halogen atom is activated by an —SO$_2$—group ortho or para thereto, is heated to form the polyethersulphone. Examples of such processes are detailed in British patent Nos. 1 153 035 and 1 078 234, and Canadian Pat. No. 847 963.

The films of the present invention generally comprise blends having a composition of 5–95 weight % (particularly 10–90 weight %) of alkylene oxide polymer and correspondingly 95–5 weight % (particularly 90–10 weight %) of aromatic polyethersulphone. Where the film is to be used for membrane separation technology, the blend preferably has a composition of 2–25 weight % of alkylene oxide polymer correspondingly 98–75 weight % of aromatic polyethersulphone.

The present invention is now illustrated by the following Examples (solubility parameters were calculated using essentially the method of Fedors, Polymer Engineering and Science, February 1974, Vol. 14, No. 2 pages 147 to 154).

EXAMPLES 1–4

10 g of aromatic polyethersulphone [RV 0.4; refractive index 1.65; solubility parameter 20.6 (MJ/m$^3$)$^{\frac{1}{2}}$] of repeat unit

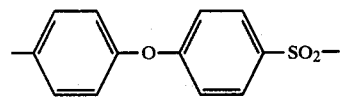

were dissolved in 50 ml N-methyl pyrrolidone. 10 g of polyethylene oxide [molecular weight about 100,000; refractive index approximately 1.52; solubility parameter 17.7 (MJ/m$^3$)$^{\frac{1}{2}}$; Polyox WSR-N-10, sold by Union Carbide Corporation] were dissolved in a mixture of 50 ml N-methyl pyrrolidone and 50 ml methylene chloride. The polyethersulphone and polyethylene oxide solutions were then mixed in various proportions to provide blends containing polyethersulphone/polyethylene oxide weight ratios of 89/11, 75/25, 57/43 and 33/67—Examples 1–4 respectively. The mixtures of Examples 1 and 2 were clear; the mixtures of Examples 3 and 4 were hazy but were clarified by adding further N-methyl pyrrolidone. The four clear solutions were then cast onto glass plates which were dried at 120° C. in air and then for 1 hour in a vacuum oven at 110° C. The films peeled from the plates were transparent and resilient at room temperature. Infra-red spectroscopic examination of the films showed an intense band at 1700 cm$^{-1}$ indicating that N-methyl pyrrolidone was present. The films were further dried overnight at 110° C. under vacuum. Infra-red examination showed that very little N-methyl pyrrolidone remained (virtual absence of a band at 1700 cm$^{-1}$). It was noticed that at 110° C., the films of Examples 1-3 were transparent while that of Example 4 was opaque. After cooling rapidly to room temperature all four films (including that of Example 4) were transparent. On reheating to 110° C., the film of Example 4 again became opaque; this process was thus reversible. The films of Examples 1-3 also showed an infra-red absorption band near 950 cm$^{-1}$ whereas in the film of Example 4 this band was split such that a new absorption band appeared near 965 cm$^{-1}$. This suggests that the polyethylene oxide component of Example 4 has crystallised because of thermal heating during infra-red spectrascopic examination.

EXAMPLE 5

An aromatic polyethersulphone (89 weight %)/polyethylene oxide (11 weight %) film prepared according to Examples 1-4 but containing a little residual N-methyl pyrrolidone was subjected to boiling water for 18 hours. Examination of the film by infra-red spectroscopy showed that N-methyl pyrrolidone had been completely removed (absence of a band near 17,000 cm$^{-1}$). Examination of the region near 3,000 cm$^{-1}$ showed that the polyethersulphone/polyethylene oxide ratio had remained substantially the same, while examination of the region near 3,600 cm$^{-1}$ showed that hardly any water had been absorbed. The film also remained transparent and resilient. It therefore appears that the water-soluble polyethylene oxide component is not affected by boiling water.

EXAMPLES 6-8

Films were prepared by a similar method to that described in Examples 1-4, using the same polyethersulphone and a different polyethylene oxide [molecular weight about 600,000; refractive index approximately 1.52; solubility parameter 17.7 (MJ/m$^3$)$^{\frac{1}{2}}$; Polyox WSR-205, sold by Union Carbide Corporation]. The films had polyethersulphone/polyethylene oxide weight ratios of 57/43, 75/25 and 89/11 —Examples .6-8 respectively. They were subjected to boiling water for 2 hours. The films remained transparent and resilient; examination by the infra-red technique described in Example 5 showed that the films were not affected by boiling water.

EXAMPLES 9-12

10 g of aromatic polyethersulphone of repeat unit

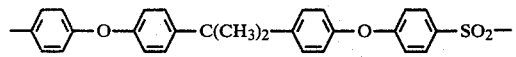

(Udel P 1700, sold by Union Carbide Corporation; refractive index approximately 1.63; solubility parameter 21.72) were dissolved in 50 ml of methylene chloride. 10 g of polyethylene oxide (Polyox WSR-205) were dissolved in 100 ml methylene chloride. The solutions were mixed in various proportions to provide blends containing polyethersulphone/polyethylene oxide weight ratios of 88/12, 75/25, 57/43 and 33/67—Examples 9-12 respectively. Phase separation occurred in each case when the solutions were mixed, but single phase solutions were obtained by adding N-methyl pyrrolidone. The four clear solutions were then cast onto glass plates as described in Examples 1-4. The films peeled from the plates were transparent and resilient.

EXAMPLES 13, 14 and COMPARATIVE EXAMPLE 15

Transparent films were prepared by a similar method to that described in Examples 1-4 using the same polyethersulphone and a different polyethylene oxide [molecular weight believed to be about 900,000; refractive index approximately 1.52; solubility parameter 17.7 (MJ/m$^3$)$^{\frac{1}{2}}$; Polyox WRPA-3154, sold by Union Carbide Corporation]. The films had polyethersulphone/polyethylene oxide weight ratios of 90/10 and 80/20— Examples 13 and 14 respectively.

The tendency of these films to absorb water was assessed as follows. Film samples (ex storage) were first weighed and their infra-red spectra recorded. These samples were then immersed for 20 seconds in distilled water at 20° C., blotted dry with paper tissues and reweighed. The procedure was then repeated after a 5 minute immersion. The following results were obtained a (see Table 1):

TABLE 1

| Ex. No. | Polyethersulphone/ polyethylene oxide wt. ratio | Wt of film sample before immersion | Wt of film sample after 20 seconds immersion | Wt of film sample after 5 minutes immersion |
| --- | --- | --- | --- | --- |
| 13 | 90/10 | 0.0360 g | 0.0360 g | 0.0365 g |
| 14 | 80/20 | 0.1390 g | 0.1395 g | 0.1400 g |

The results in Table 1 show that substantially all excess surface water (i.e. non-absorbed water) can be removed from the films by a mild procedure (i.e. blotting) which will not affect the level of truly absorbed water, provided that an accuracy of not better than about ±2% is being sought.

Samples of the above films and a control sample of a film made solely from the polyethersulphone (Comparative Example 15) were dried overnight at 70° C. in a vacuum oven and weighed. The thickness of each film was also measured.

TABLE 2

| Ex. No. | Polyethersulphone/ polyethylene oxide wt ratio | Thickness of film sample | Wt of film sample ex. vac. oven before immersion | Wt of film sample after 5 minutes immersion | Wt of film sample after 3 hours immersion | Wt of film sample after 20 hours immersion |
| --- | --- | --- | --- | --- | --- | --- |
| 13 | 90/10 | 20 micron | 0.0354 g | 0.0362 g | 0.0360 g | 0.0355 g |
| 14 | 80/20 | 23 micron | 0.1385 g | 0.1392 g | 0.1405 g | 0.1395 g |
| 15 | 100/0 | 52 micron | 0.2520 g | 0.2550 g | 0.2550 g | 0.2545 g |

The films were then immersed in water at 20° for 5 minutes, removed, blotted and reweighed. This was repeated after 3 hours immersion and also after 20 hours immersion. The following results were obtained (see Table 2).

It is thus apparent from the results in Table 2 that the film samples corresponding to Examples 13 and 14 did not absorb water (any slight increases in weight being within the scope of experimental error—see Table 1). This was confirmed by the observation that the infra-red spectra of the blotted films, recorded after 20 hours immersion, were identical with those of the original films before water immersion (thereby enabling one to discount the possibility of the lack of any significant weight increases being due to polyethylene oxide having been leached out of the films and replaced with an equivalent weight of water). It was noticed during these experiments, however, that whereas the control polyethersulphone film sample (Example 15) was not wetted by water, the film samples according to the invention (Examples 13 and 14) were easily wetted by water.

The contact angles of the film surfaces to water of the film samples were measured in the following way. Each film was stretched flat on a matt black table using double-sided adhesive tape. Small drops of distilled water were placed on the film and a droplet was illuminated and viewed using a reflecting goniometer device. Five values of contact angle for each film sample were taken. The results are shown in Table 3.

TABLE 3

| Ex. No. | Polyether-sulphone/ polyethylene oxide wt ratio | Contact angle observed (five values) | Mean value of contact angle |
|---|---|---|---|
| 13 | 90/10 | 55°, 50°, 60°, 57°, 54° | 54° |
| 14 | 80/20 | 45°, 40°, 40°, 40°, 40° | 40° |
| 15 | 100/0 | 70°, 65°, 75°, 70°, 72° | 70° |

EXAMPLE 16

1 g of the polyethylene oxide used in Examples 13 and 14 was dissolved in 10 g methylene chloride. To the stirred solution was added a solution of 9 g of the aromatic polyethersulphone used in Examples 1–4 in 40 ml dimethyl formamide, thereby providing a composition having a polyethersulphone/polyethylene oxide weight ratio of 90/10. The appearance of the mixture was hazy but the addition of a further 25 ml of dimethyl formamide resulted in the formation of a clear solution. The solution was then cast onto a glass plate and dried overnight in a vacuum oven at 90° C. Infra-red spectroscopic examination showed that all the solvent had been removed. Three small samples of the film were respectively subjected for 24 hours to boiling water, boiling dilute NaOH (2 g NaOH per 100 ml water) and boiling dlute HCl (5 ml conc. HCl per 100 ml water). Their infra-red spectra were then examined and found to be unchanged from the untreated film, indicating that the film is not affected by boiling water, boiling dilute acid and boiling dilute alkali.

I claim:

1. A polymer composition in the form of a film which composition comprises a compatible blend of an alkyl oxide polymer not containing units derived from a cyclic ester and an aromatic polyethersulphone, wherein said alkylene oxide polymer is an ethylene oxide homopolymer or copolymer containing only ethylene oxide and one or more different alkylene oxide units, has a molecular weight of at least 100,000, and is water-soluble.

2. A polymer composition according to claim 1, wherein the alkylene oxide polymer contains at least 50 mole of ethylene oxide units.

3. A polymer composition according to claim 1 wherein the polyethersulphone has the repeat unit

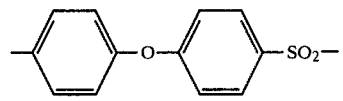

or the repeat unit

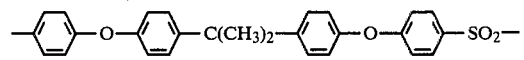

alone or in conjunction with other repeat units.

4. A polymer composition according to claim 1 wherein the compatible blend has a composition of 5–95 weight % of alkylene oxide polymer and correspondingly 95–5 weight % of aromatic polyethersulphone.

5. A polymer composition according to claim 1 wherein the compatible blend has a composition of 2–25 weight % of alkylene oxide polymer and correspondingly 98–75 weight % of aromatic polyethersulphone.

6. A polymer composition according to claim 1 in the form of a transparent film.

7. A polymer composition according to claim 1 wherein the film has a contact angle of its surface to water of $\leq 60°$.

8. A polymer composition according to claim 1 in the form of a porous or semi-permeable film.

9. A polymer composition according to claim 8 in the form of a porous or semi-permeable film used in a membrane separation system or as the encapsulating membrane in a system for the sustained and/or predictable release of a biologically active species in unit dosage form.

10. A process for the production of a polymer composition in the form of a film according to claim 8 which process comprises forming a film by solvent casting a composition comprising a blend of the alkylene oxide polymer not containing units derived from a cyclic ester and an aromatic polyethersulphone but allowing some of the solvent casting medium to remain in the film, and leaching the film with a liquid which is miscible with at least one component of the solvent casting medium and is also a non-solvent for the polymers.

* * * * *